(12) United States Patent
Terao (10) Patent No.: US 8,700,582 B2
(45) Date of Patent: Apr. 15, 2014

(54) DOCUMENT HANDLING HISTORY MANAGEMENT SYSTEM AND METHOD

(75) Inventor: Taro Terao, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 515 days.

(21) Appl. No.: 11/872,152

(22) Filed: Oct. 15, 2007

(65) Prior Publication Data

US 2008/0183756 A1   Jul. 31, 2008

(30) Foreign Application Priority Data

Jan. 31, 2007 (JP) .................................. 2007-21460

(51) Int. Cl.
*G06F 7/00* (2006.01)
*G06F 17/30* (2006.01)
*G06F 19/00* (2011.01)

(52) U.S. Cl.
CPC ........ *G06F 17/30076* (2013.01); *G06F 19/322* (2013.01); *G06F 17/30011* (2013.01); *G06F 19/3487* (2013.01)
USPC .......................................... 707/695; 715/229

(58) Field of Classification Search
CPC ............ G06F 17/322; G06F 17/30011; G06F 19/3487
USPC .......................................... 707/695; 715/229
See application file for complete search history.

(56) References Cited

U.S. PATENT DOCUMENTS

| | | | | |
|---|---|---|---|---|
| 5,655,119 A | * | 8/1997 | Davy | 707/999.2 |
| 2003/0079175 A1 | * | 4/2003 | Limantsev | 715/500 |
| 2005/0131940 A1 | * | 6/2005 | Le Sauze et al. | 707/104.1 |
| 2005/0283492 A1 | * | 12/2005 | Schmitt et al. | 707/100 |
| 2007/0150948 A1 | * | 6/2007 | De Spiegeleer | 726/22 |

FOREIGN PATENT DOCUMENTS

JP      11-249777 A    9/1999

* cited by examiner

*Primary Examiner* — Cheyne D Ly
(74) *Attorney, Agent, or Firm* — Sughrue Mion, PLLC (57) ABSTRACT

A document handling history management system, which includes: a first calculation section that calculates a first value based on a document which is an object of referencing operation; an operation history information generation section that generates operation history information that includes the first value; a second calculation section that calculates a second value based on the operation history information; a referencing information generation section that generates referencing information of the document, the referencing information being used for the referencing operation and including the second value; a reading section that reads first attribute information of the document, the first attribute information being to be rewritten to second attribute information when the referencing operation of the document is performed; a storing section that stores setting information in the first attribute information; and a rewriting section that rewrites the second attribute information to the first attribute information upon termination of the referencing operation.

14 Claims, 8 Drawing Sheets

DOCUMENT HANDLING HISTORY MANAGEMENT SYSTEM AND METHOD

CROSS-REFERENCE TO RELATED APPLICATION

This application is based on and claims priority under 35 USC 119 from Japanese Patent Application No. 2007-21460 filed on Jan. 31, 2007.

BACKGROUND

1. Technical Field

The present invention relates to a document handling history management system, a document handling history management method, a recording medium storing a document handling history management program, and a data signal embodied in a carrier wave.

2. Related Art

When content of a file is read through referencing processing of a document prepared by using an application program, it is desirable that the status of the document after the referencing processing be not changed from the status before the referencing processing, since the document itself is not updated or altered. However, if some application program is used to implement the referencing processing of a document, the status of the document may be changed between before and after the referencing processing.

For example, the apparatus identification number for the preparer (the apparatus identification number for the updater), the information about preparation time and date (update time and date), and the like, which is set as the attribute information for the document subjected to the referencing processing may be changed. This is because, although the document itself is not edited or updated, the management apparatus that managed the document recognizes as if the document were updated, and thus history information indicating that it has been updated is prepared.

SUMMARY

An aspect of the present invention provides a document handling history management system, which includes: a first calculation section that calculates a first value by applying a computing equation to a document which is an object of referencing operation; an operation history information generation section that generates operation history information that includes the first value calculated by the first calculation section; a second calculation section that calculates a second value by applying the computing equation to the operation history information generated by the operation history information generation section; a referencing information generation section that generates referencing information of the document, the referencing information being used for the referencing operation and including the second value calculated by the second calculation section; a reading section that reads first attribute information of the document, the first attribute information being to be rewritten to second attribute information when the referencing operation of the document is performed based on the referencing information generated by the referencing information generation section; a storing section that stores setting information that is set in the first attribute information of the document read by the reading section; and a rewriting section that rewrites the second attribute information to the first attribute information using the setting information stored in the storing section upon termination of the referencing operation.

BRIEF DESCRIPTION OF THE DRAWINGS

An exemplary embodiment of the present invention will be described in detail based on the following figures, wherein.

DETAILED DESCRIPTION

Hereinbelow, one exemplary embodiment of the document handling history management system, the document handling history management method, the recording medium storing the document handling history management program, and the data signal embodied in the carrier wave pertaining to the present invention will be described in detail with reference to the attached drawings.

Figure 1:
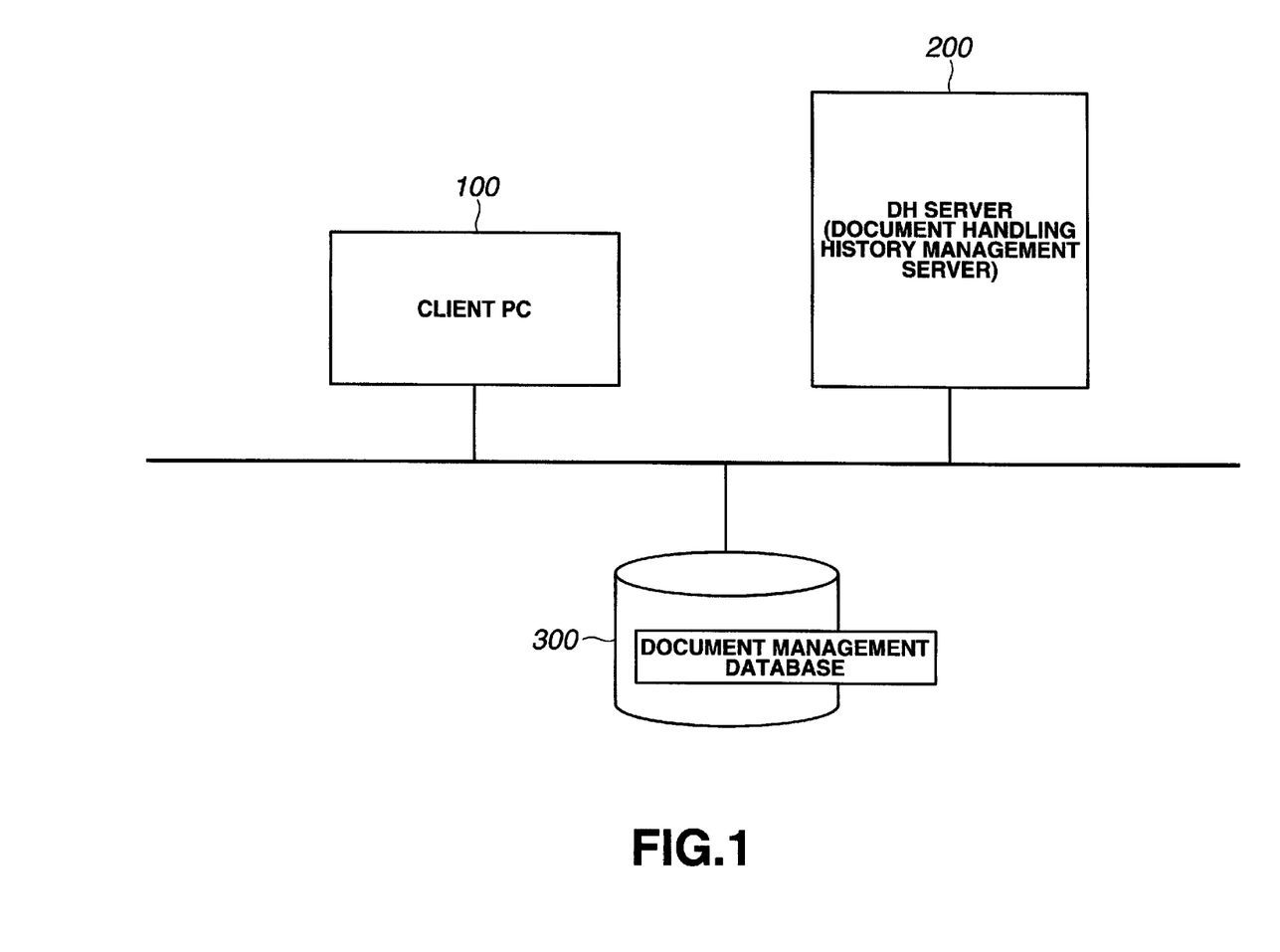
FIG. 1 is one example of configuration diagram for a document handling history management system configured by applying the document handling history management system and program therefor pertaining to the present invention.

FIG. 1 is one example of configuration diagram for a document handling history management system configured by applying the document handling history management system, the document handling history management method, the recording medium storing the document handling history management program, and the data signal embodied in the carrier wave pertaining to the present invention.

In this document handling history management system as shown in FIG. 1, a document handling history management server 200 (hereinafter referred to as a "DH (Document History) server 200") that manages the history information about the handling performed on an electronic document (hereinafter referred to as a "document") prepared using an application program, such as a document preparation application program, a table computation application program, or the like, as the "handling history information"; a client PC 100 in which the application program for preparing such document are installed; and a document management database 300 that manages and stores a prepared document are connected to one another through a communication line.

This document handling history management system is a system that, in performing handling, such as referencing, reading, editing, printing, copying, scanning, discarding, or the like, on a document managed by the document management database 300, allows the handling history based on the handling content to be managed, whatever application program has been used, regardless of the type of application program associated with that document.

In the following description of the present exemplary embodiment, an example in which handling is performed on a document managed on the document management database 300 is given, however, the system is not limited to such example. And it may be configured so as to perform handling on the document stored on the client PC 100. In other words, the management location for the document to be handled may be on any network node.

The client PC 100 is capable of preparing a reference, which provides referencing information for referencing a document under management; the prepared reference includes information for identifying the corresponding document; and by using the reference, it is made possible to handle the document. In addition, this client PC 100 implements correction processing of the document to be handled such that the DH server 200 can generate handling history information based on the handling contents and manage it.

The correction processing mentioned here may be defined as the processing for returning the information that is rewritten through the referencing and reading the document to be handled, to the information before the rewriting.

The DH server 200 generates handling history information for the handling performed on a document, and manages it. Generation of this handling history information is carried out with the document being uploaded on the DH server 200. In other words, for any document for which correction processing is required on the client PC 100, the correction processing for the document is implemented before handling history information is generated.

Next, the method for preparing a reference for a document prepared on the client PC 100 and the method for generating the handling history information that is to be managed by the DH server 200 will be described with reference to FIG. 2A to FIG. 2E. In a case where a reference is newly prepared, the handling history information for the document as an object of preparation of the reference is generated in the course of the preparation of the reference.

Therefore, herein both the method for preparation of a reference and the method for generation of handling history information will be collectively described.

From the client PC 100, a document that is managed on the document management database 300 and that is to be handled is designated, and an instruction for preparing a reference for that document is given. Examples of the method for giving an instruction for preparing a reference that is to be used at this time include the method for giving an instruction by selecting the "reference preparation" from the context menu.

At this time, when an instruction for preparing a reference is given, this document is uploaded onto the DH server 200. The DH server 200 applies the hash function, such as "SHA-256", to the entire document for which preparation of a reference is instructed, for computing a hash value and outputting it. The hash value obtained by this computation provides a uniquely corresponding relationship between it and the document. The hash value obtained at this time is called the "document hash value".

Not to mention, the unit that can use the hash function to compute the hash value for outputting it is not limited to the DH server 200, thus the system may be adapted such that the hash value is computed in a particular location where the document exists.

FIG. 2A to FIG. 2E are drawings illustrating the document hash value that is computed in preparing the reference, and the status of the reference after being prepared.

Figure 2A:
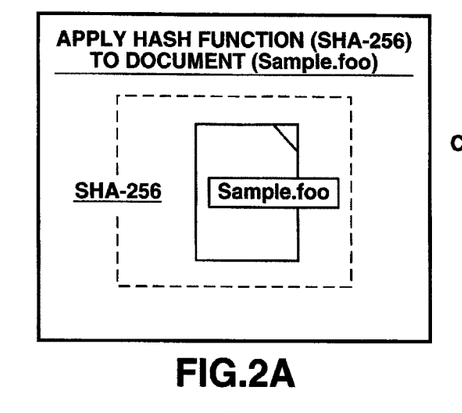
FIG. 2A to FIG. 2E are drawings illustrating the document hash value that is computed in preparing a reference, and the status of the reference after handling history information is prepared.
Figure 2B:
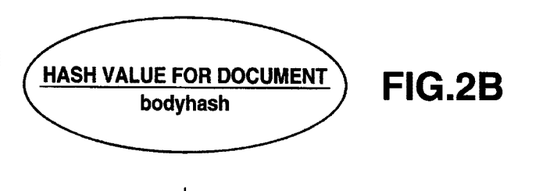
Figure 2C:
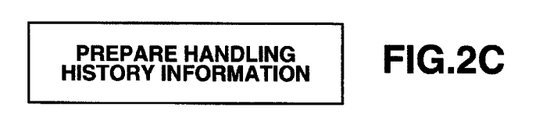
Figure 2D:
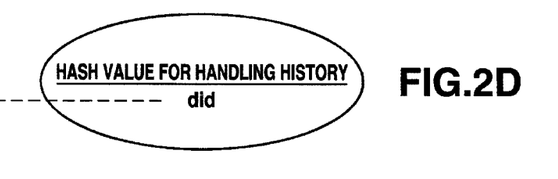
Figure 2E:
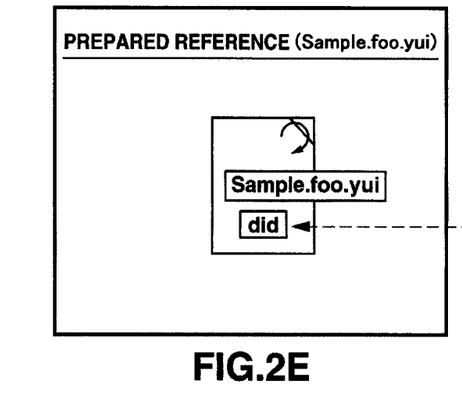

FIG. 2A is a drawing illustrating that the hash function called "SHA-256" is applied to a document named "sample.foo", and FIG. 2B gives the document hash value "bodyhash" that is computed by applying the hash function "SHA-256" to the document "sample.foo". In a case where the document is subjected to editing/updating, this document hash value before the editing is different from that after the editing.

In this way, when the document hash value "bodyhash" for the document is computed, the document is then bound, and handling history information in an XML (Extensible Markup Language) format including the document hash value "bodyhash" computed is prepared. One example of this handling history information is given below.

At the left end of each line of the handling history information as given below, the line number to be used for explanation is given.

```
01 <doc>
02 <body>bodyhash</body>
03 <base>          </base>
04 <info>
05 <user>user_A</user>
06 <time>time_A</time>
07 <method>create</method>
08 </info>
09 </doc>
```

This handling history information provides information in an XML format that is enclosed by the <doc> tag in the 01st line and the </doc> tag in the 09th line. As an element in the <body> tag as given in the 02nd line, the document hash value "bodyhash" computed by applying the hash function to the document is designated, and as an element in the <base> tag in the 03rd line, the value of "did" computed by implementing the computation processing later described is designated.

This value "did" is information computed from the handling history information for the document having the document hash value "bodyhash", i.e., the element in the <body> tag as given in the 02nd line, and is used as information for managing the handling history for the document.

In addition, between the <info> tag in the 04th line and the </info> tag in the 08th line, the "user_A", which is the information on the user who handled the document, is designated as an element in the <user> tag in the 05th line; the "time_A", which is the information on the time when the document is uploaded onto the DH server 200, is designated as an element in the <time> tag in the 06th line; and the information that indicates the type of the handling that is performed on the document is designated as an element in the <method> tag in the 07th line.

In addition, elements that can be designate to the <method> tag in the 07th line include "create", which indicates a handle for newly preparing a reference for a document (in the above example, handle for selecting the "preparation of reference" from the context menu); "modified", which indicates that updating/editing is performed to the document corresponding to the reference; "not modified", which indicates that referencing/reading is performed to a document; "printed", which indicates that printing is performed to a document; and the like. In this case, because a reference is newly prepared, "create" is designated as the element in the above-mentioned <method> tag.

In a case where the element in the <method> tag as given in the 07th line is "create", in other words, in a case where handling history information in an XML format is newly prepared, the element in the <base> tag is empty. This is because the element in the <base> tag is to be a value given by computing the handling history information that is already prepared.

In this way, in the course of preparing a reference, handling history information in an XML format is newly prepared.

Then, in order to prepare a reference, the hash function, which computes the document hash value "bodyhash" as the element in the <body> tag in the 02nd line of the handling history information in an XML format, is used to compute the hash value "did" for the handling history information. In the example as given above, by using the hash function "SHA-256" for hash computation of the handling history information in an XML format that is enclosed by the <doc> tag in the 01st line and the </doc> tag in the 09th line, the hash value "did" is computed. The hash value "did" obtained at this time is referred to as the "history hash value".

And, by transferring the computed history hash value "did" to the client PC 100, the client PC 100 prepares a reference in which the history hash value "did" is set. FIG. 2A to FIG. 2E illustrate an example in which a reference denoted by the extension "yui" is prepared. In addition, in FIG. 2E, a rotating arrow is provided at upper right of the icon for indicating that the icon represents the reference.

The reference thus prepared is placed on any of the client PC 100, the DH server 200, and the document management database 300 such that, by using this reference, the document on the document management database 300 can be simply referenced.

Next, the processing of identifying the document by using the reference prepared as described above will be described in detail.

First, the history hash value "did" included in the reference is taken out, and the handling history information associated with the history hash value "did" is identified. The handling history information to be identified at this time is managed by the DH server 200, being correlated to the history hash value "did".

Then, the element "bodyhash", which is designated in the <body> tag in the identified handling history information, is acquired. This element "bodyhash" is a document hash value, and the DH server 200 identifies the document "sample.foo" corresponding to this document hash value "bodyhash". The name of this document, i.e., "sample.foo", indicates that this document is a document prepared with the "foo" application program.

As described above, the document is identified from the prepared reference.

Next, the processing of referencing/reading handling of the document identified by using the reference will be described in detail.

With the client PC 100 that uses the reference to perform referencing/reading of the document, the item information to be altered by the application program associated with that document is read. When the item information to be altered is read, the set value given to the item information read is temporarily stored. In this status, the application program is activated for performing referencing/reading of the document.

And, in a case of terminating the handling of referencing/reading the document identified by using the reference, the termination processing for the handling of referencing/reading with the application program is implemented, which is then followed by implementing the correction processing, which rewrites the previously read item information with the use of the set value that is temporarily stored. In other words, the set value given to the item information is rendered equal to that before the referencing/reading handling, and the document after this correction processing is uploaded onto the DH server 200.

This item information is information representing the alterable item that is set for each application program, for example, time stamp information, or apparatus identification information (for example, MAC (Media Access Control) address) that identifies the handler that performs the handling, and is managed in association with the application program.

Examples of such correction processing will be described with reference to FIG. 3A to FIG. 3C.

Figure 3A:
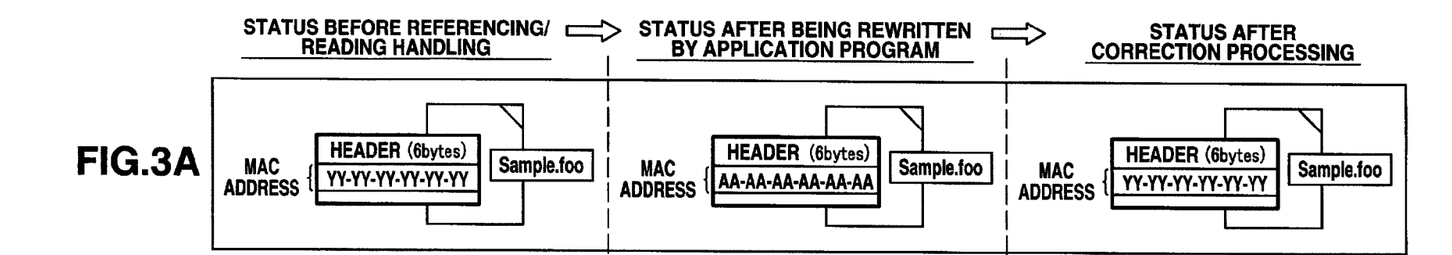
FIG. 3A to FIG. 3C illustrate examples of set information given in the three statuses, i.e., the status before the referencing/reading handling; the status after the rewriting by the application program; and the status after the correction processing, respectively.
Figures 3B, 3C:
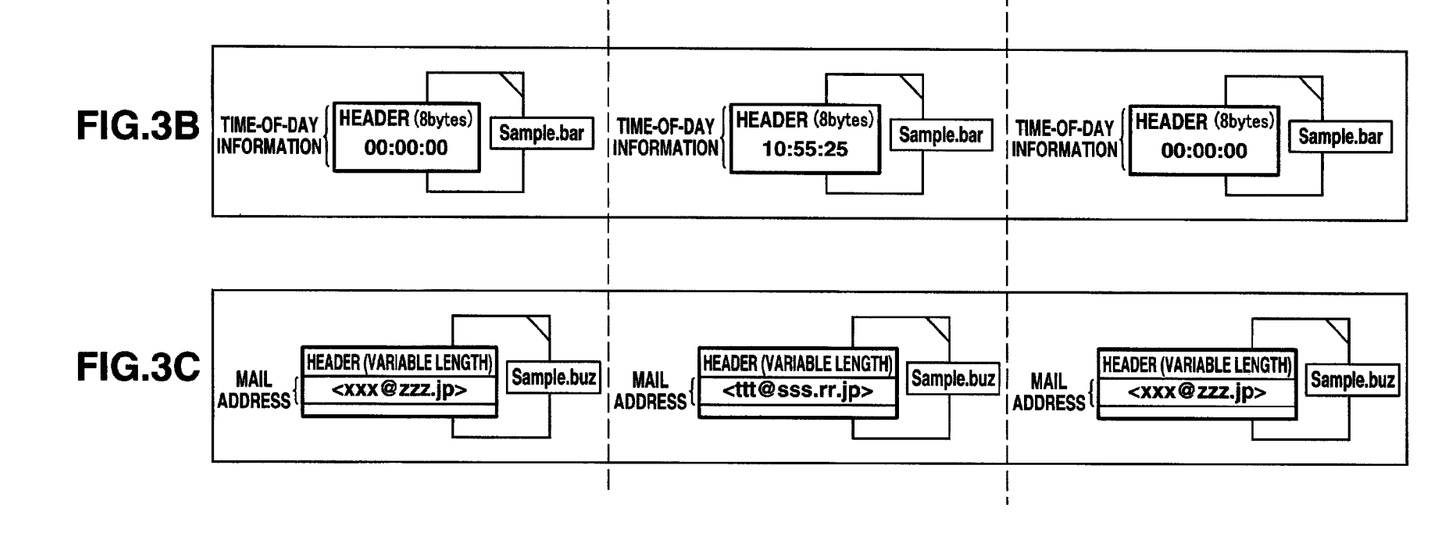

FIG. 3A to FIG. 3C illustrate set information given in the three statuses, i.e., the status before the referencing/reading handling; the status after the rewriting by the application program; and the status after the correction processing, respectively.

FIG. 3A illustrates the document "sample.foo" correlated to the document application program "foo"; FIG. 3B illustrates the document "sample.bar" correlated to the document application program "bar"; and FIG. 3C illustrates the document "sample.buz" correlated to the document application program "buz".

The document "sample.foo" as illustrated in FIG. 3A has a header region of a fixed length of 6 bytes (48 bits). In this region, the MAC (Media Access Control) address, which is the identification number of the apparatus, i.e., the handler is given.

This MAC address is given as item information that is to be rewritten by the document application program "foo", and it is indicated that the MAC address before referencing/reading handling is "YY-YY-YY-YY-YY-YY". In addition, when referencing/reading handling of the document "sample.foo" is performed, the MAC address is rewritten by the application program into "AA-AA-AA-AA-AA-AA". And, just before terminating the document application program "foo", the correction processing that overwrites the MAC address with the MAC address before the referencing/reading handling, i.e., "YY-YY-YY-YY-YY-YY" is implemented.

The document "sample.bar" as illustrated in FIG. 3B has a header region of a fixed length of 8 bytes (64 bits). In this region, the time-of-day information in a 64-bit format is given.

This time-of-day information is given as item information that is to be rewritten by the document application program "bar", and it is indicated that the time-of-day information before referencing/reading handling is "00:00:00". In addition, it is indicated that, with the document "sample.bar" being referenced/read, this time-of-day information is rewritten into "10:55:25". Just before terminating the document application program "bar", the correction processing that overwrites the time-of-day information with the time-of-day information before the referencing/reading handling, i.e., "00:00:00" is implemented.

The document "sample.buz" as illustrated in FIG. 3C has a header region of a variable length in the head portion of the document. In the header region, the mail address, which is a user identifier for identifying the user, is given. As an example of this mail address, i.e., the user identifier, "xxx@zzz.jp" is given in FIG. 3C with symbols of "<" and ">" being given before and after the mail address, respectively.

The mail address before referencing/reading handling is "xxx@zzz.jp", and when referencing/reading handling of the document "sample.buz" is performed. This mail address is rewritten into "ttt@sss.rrjp" by the document application program "buz". And, just before terminating the document application program "buz", the correction processing that overwrites the mail address with "xxx@zzz.jp", which is the mail address before rewriting, is implemented.

Such correction processing is implemented, and the client PC 100 uploads the document after the correction onto the DH server 200. Thus, the DH server 200 prepares handling history information for the document uploaded. One example of the handling history information prepared at this time will be given below.

First, the hash function, such as "SHA-256", is applied to the entire document uploaded by the client PC 100, to compute the document hash value "bodyhash2". Because the type of the contents of the handling performed by the client PC 100 is reading/referencing handling, it is verified that the computed document hash value "bodyhash2" is identical to the document hash value "bodyhash" before the referencing/reading, and handling history information in an XML format as given below is prepared.

Incidentally, in a case where the document hash value "bodyhash2" computed is different from the document hash value "bodyhash" before the handling, it means that a type of handling other than referencing/reading was performed on the document.

```
01 <doc>
02 <body>bodyhash</body>
03 <base>did</base>
04 <info>
05 <user>user_A</user>
06 <time>time_B</time>
07 <method>not modified</method>
08 </info>
09 </doc>
```

In this handling history information, "did", which is the element in the <base> tag in the 03rd line, is the history hash value computed by applying the hash function to the handling history information before referencing/reading handling of the, and is designated to the reference. In addition, "time_B", which is the element in the <time> tag in the 06th line, indicates the time when the document was uploaded onto the DH server 200. As the element in the <method> tag in the 07th line, "not modified", which indicates that only the referencing/reading handling was performed, and editing and altering of the document were not performed, is given.

The handling history information generated as described above is managed by the DH server 200 for each particular document. And, this DH server 200 further applies the hash function, such as "SHA-256", to the generated handling history information, thereby computing the history hash value "did2".

In addition, the DH server 200 sends the computed history hash value "did2" to the client PC 100 that performs the referencing/reading handling, and the client PC 100 updates the history hash value set for the reference with the history hash value "did2" received.

Figure 6:
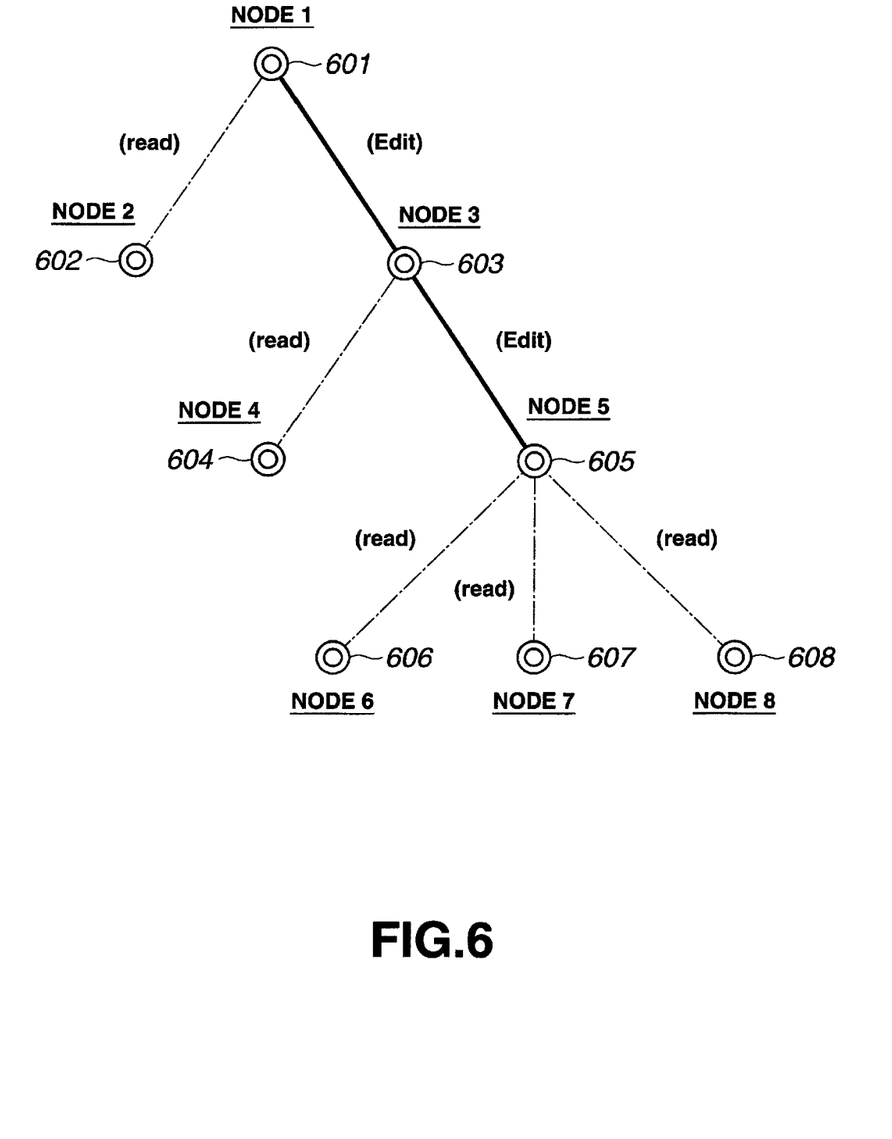
FIG. 6 is a drawing that adopts a tree structure to represent the handling history for the document that is handled using the reference.

Thus, if the reference is used to handle the document, the reference is updated on the basis of the contents of the handling performed on that document. In addition, by using the reference for repetitively performing the handling of the document, a tree structure as shown in FIG. 6 is built for managing the handling history.

Figure 4:
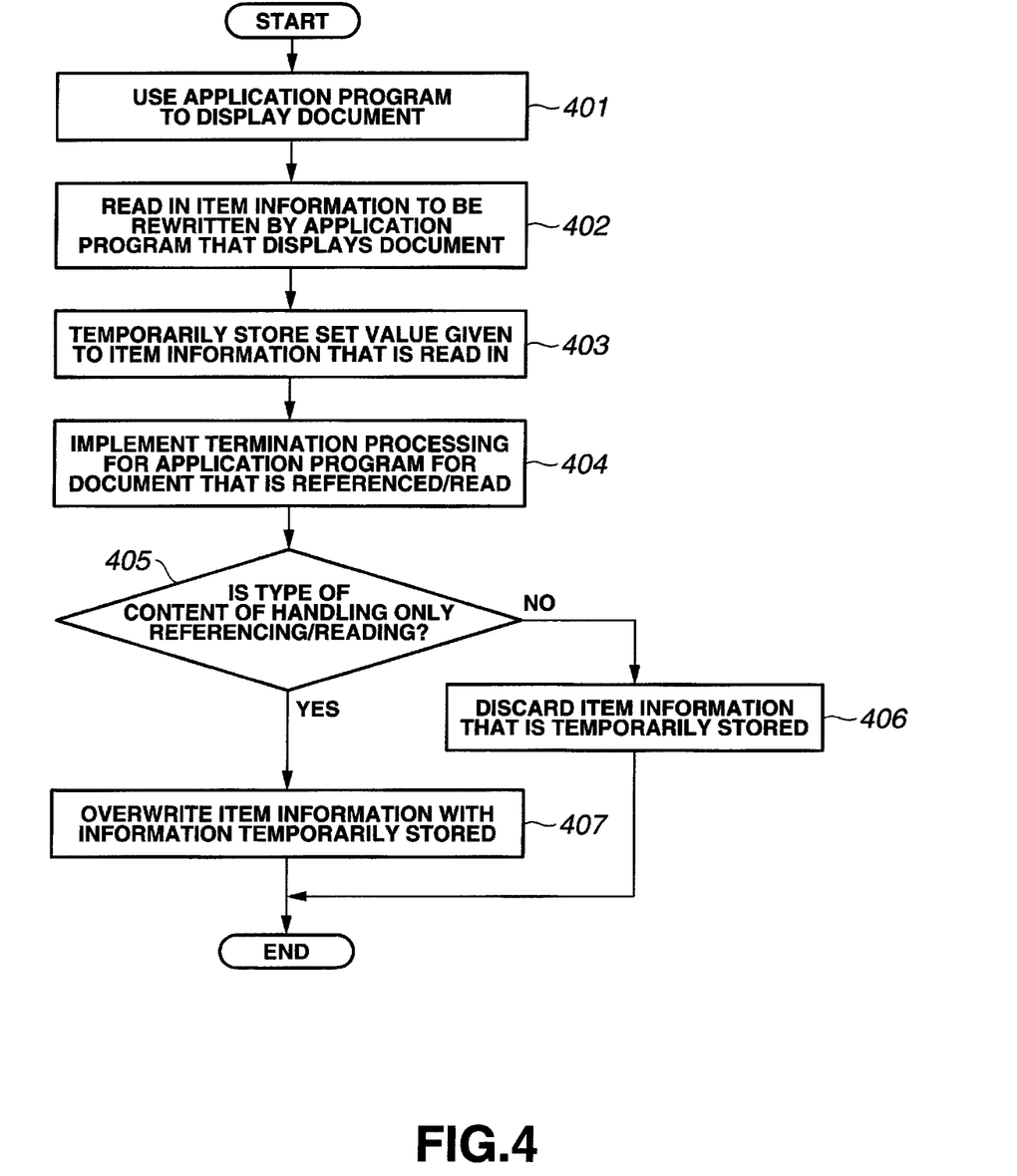
FIG. 4 gives one example of flowchart illustrating the detailed flow of the correction processing.

FIG. 4 gives one example of flowchart illustrating the detailed flow of the correction processing.

In FIG. 4, upon designating the document to be referenced/read by using the reference, the processing is started, and the document is displayed by using the application program corresponding to that document (401). Then, the item information to be rewritten by the application program that displays the document is read (402), and the information that is set for the item information read is temporarily stored (403).

In the example as given in FIG. 3A, the "foo" application program is to be used to rewrite the MAC address of a fixed length of 6 bytes that is provided in the header region of the document "sample.foo" to be referenced/read, thus the MAC address before this referencing/reading is read and temporarily stored.

And, when the termination processing for the application program for the referenced/read document is implemented (404), the type of the contents of the handling performed on the document is determined (405). In a case where the type of the contents of the handling is rewriting processing, such as editing or updating (NO at 405), the information that is temporarily stored is discarded (406).

On the other hand, in a case where the type of the contents of the handling performed on the document is referencing/reading (YES at 405), the information rewritten by the application program that reads the document is overwritten with the information temporarily stored (407) to correct the rewritten information.

Figure 5:
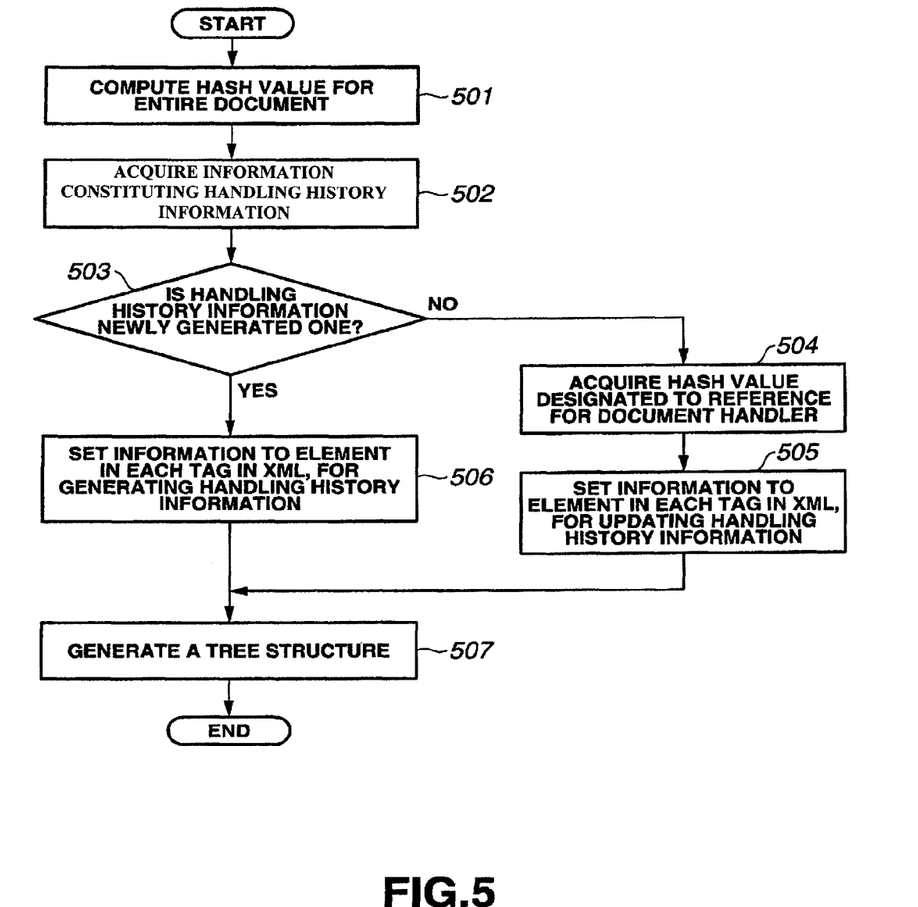
FIG. 5 gives one example of flowchart illustrating the detailed flow of the processing for generating handling history information.

For the document corrected by such correction processing, handling history information is generated based on the flowchart as given in FIG. 5.

FIG. 5 gives one example of flowchart illustrating the detailed flow of the processing for generating handling history information.

After the correction processing is implemented through the flowchart as given in FIG. 4 and the document is uploaded onto the DH server, the processing for applying the hash function to the entire document correction-processed is started and the document hash value is computed (501). In a case of the above example, the document hash value "bodyhash" is computed and obtained.

Next, the time-of-day information and the information about the handling contents that constitute the handling history information are acquired (502). These types of information can be acquired not only as system information, but also from the client PC.

Then, it is determined whether the handling history information to be generated is newly prepared one (503). When it is determined to be newly prepared one (YES at 503), the acquired information and the computed document hash value are set as an element in the pertinent tags in an XML format, respectively, whereby handling history information is generated (506).

On the other hand, in a case where the handling history information is not newly prepared one (NO at 503), for example, in a case where the reference is used for reading/referencing the document, the history hash value (the value of "did" in the above example) that is designated to the reference for identifying the document for which handling history information is to be prepared, is acquired (504), and this history hash value, the acquired time-of-day information, and the like, are set as an element in the pertinent tags in an XML format, respectively, for updating the handling history information (505).

And, on the basis of the prepared handling history information, a tree structure as shown in FIG. 6 is prepared (507).

FIG. 6 is a tree structure showing the handling history for the document handled by using the reference.

This tree structure is configured by connecting between nodes representing the history information, which is information about the history of the handled document, and is built on the basis of the history hash value included in the reference.

First, when a reference is newly prepared, a node 1 (601) disposed at the topmost level is generated. To this node 1 (601), the history hash value computed at the time of preparing the reference is designated, and in the above example, this history hash value is "did".

Next, when referencing/reading handling of the document is performed using the reference to which this history hash value "did" is designated, a node 2 (602) connected to the node 1 (601) in which the history hash value is set is generated, and disposed at a level lower than the node 1(601). To this node 2 (602), in the same manner as that for the node 1 (601), the history hash value computed by applying the hash function is designated. In the above example, the history hash value after the correction processing implemented for the document for which the referencing/reading handling is performed is designated.

In this way, the tree structure is configured.

A node 3 (603) provides history information indicating that the document corresponding to the reference for the node 1 (601) is subjected to editing handling. A node 4 (604) provides history information indicating that the document corresponding to the reference for the node 3 (603) is subjected to referencing/reading handling. In addition, a node 5 (605) provides history information indicating that the document corresponding to the reference for the node 3 (603) is subjected to editing handling. A node 6 (606), a node 7 (607), and a node 8 (608) provide history information indicating that the document corresponding to the reference for the node 5 (605) is subjected to referencing/reading handling.

Figure 7:
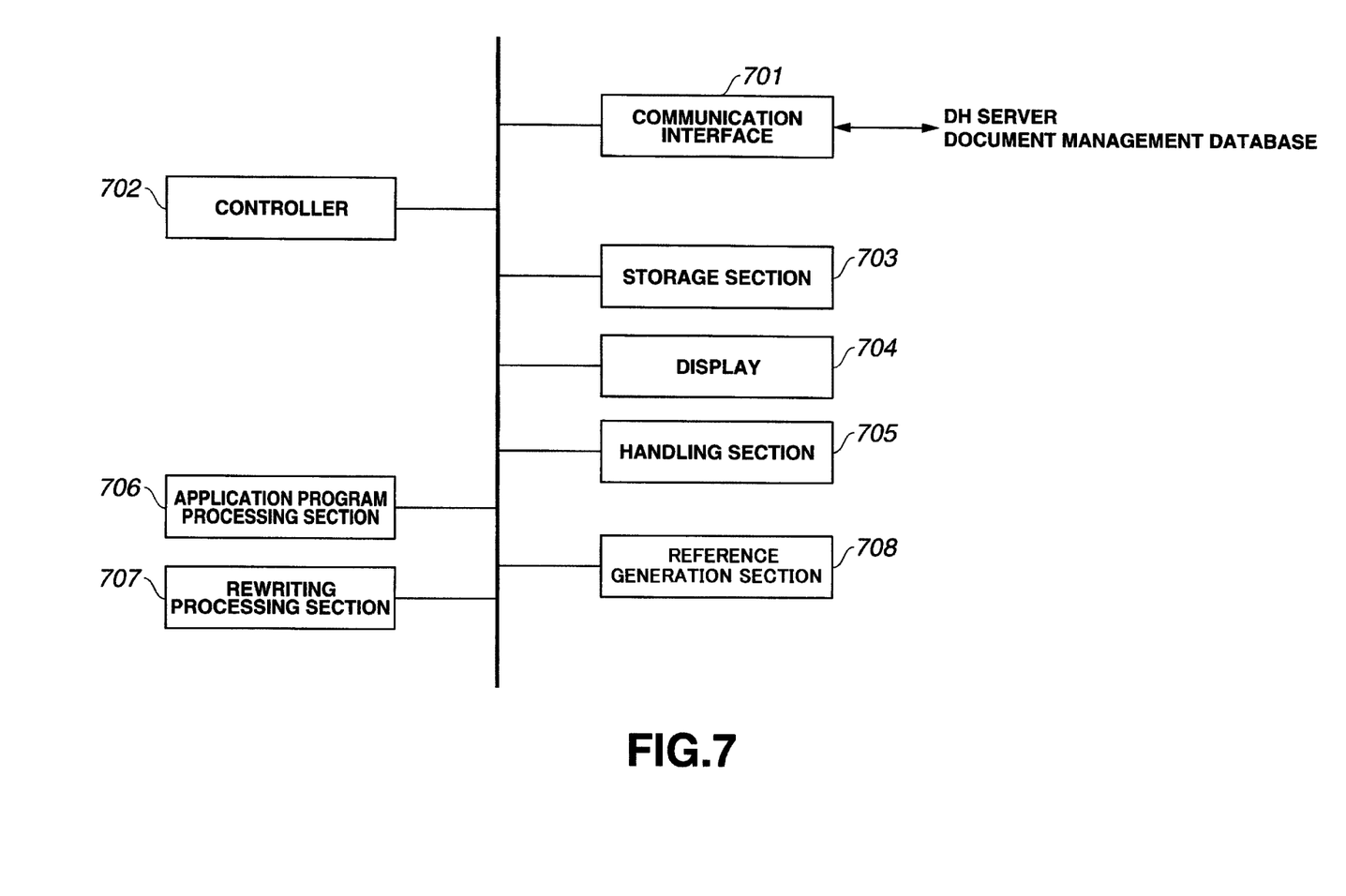
FIG. 7 is one example of block diagram illustrating the configuration of the client PC.

FIG. 7 is one example of block diagram illustrating the detailed configuration of the client PC 100 as shown in FIG. 1.

In FIG. 7, the client PC 100 comprises a communication interface 701, a controller 702, a storage section 703, a display 704, a handling section 705, an application program processing section 706, a rewriting processing section 707, and a reference generation section 708. The client PC 100 prepares a reference for referencing/reading handling of a document, and implements the correction processing of the document that is subjected to referencing/reading handling.

When a handling section 705 comprising a keyboard, a pointing device, and the like, is used to give an instruction for preparing a reference for a document managed by a document management database, or the like, the reference generation section 708 prepares a reference. This reference is prepared by communication with the DH server 200 connected through the communication interface 701.

In other words, the DH server 200 prepares handling history information in the course of preparing the reference.

The handling section 705 handles this reference prepared by the reference generation section 708, whereby the document corresponding to the reference is displayed on the display 704 with the application program processing implemented by the application program processing section 706, in order to make the referencing/reading handling possible. At this time, the controller 702 reads the item information for each application program stored in the storage section 703 or the DH server 200 connected through the communication interface 701, and temporarily stores the set information given to the document for the item information into the storage section 703.

Then, when the application program processing by the application program processing section 706 is terminated, after the controller 702 confirms that the contents of the handling of the document are only the referencing/reading handling, the rewriting processing section 707 overwrites the item information for the document with the set information stored in the storage section 703 for rewriting the information.

Figure 8:
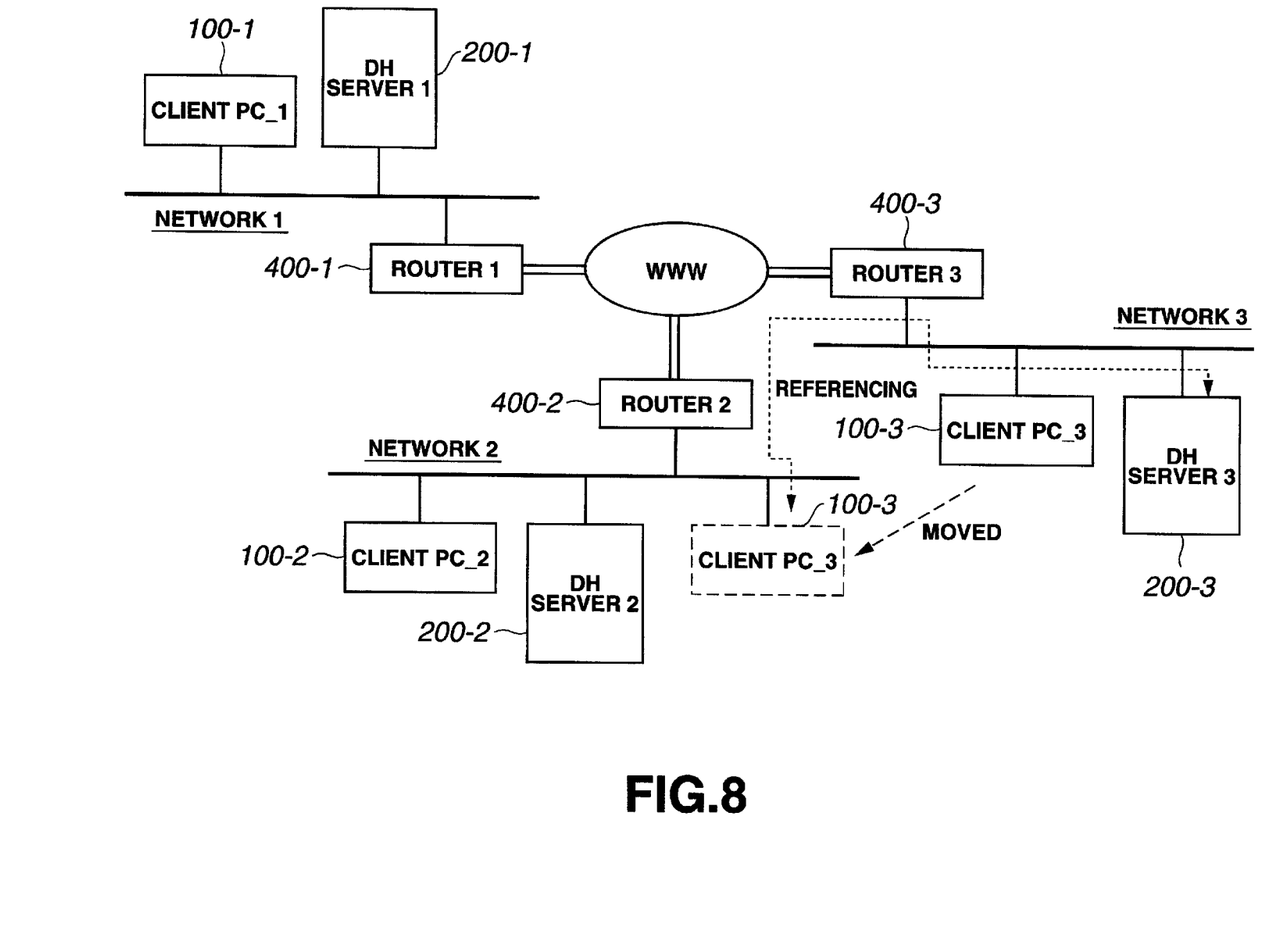
FIG. 8 is one example of diagram for another system configuration that is configured by applying the document handling history management system and program therefor pertaining to the present invention.

As the configuration of the present invention, besides the configuration in which, as shown in FIG. 1, the client PC 100, the DH server, and the document management database constitute the same network, a configuration in which, as shown in FIG. 8, a plurality of networks in which these apparatuses are connected as the network nodes may be adopted. FIG. 8 provides an example in which the document to be handled is not managed in the document management database, but stored in the individual client PCs 100.

Each network is connected to the web network through the router provided for each network. The DH server provided in each network manages the identification information for identifying the client PC 100 that manages the document for which handling history information is prepared, and manages the handling history information for the identification information.

In other words, even when the client PC 100 is moved onto any of the other network, the DH server that manages the identification information for the client PC 100 generates handling history information, and the client PC 100 is unifiedly managed.

FIG. 8 provides an example case where the client PC 3 (100-3) for which the identification information is managed by the DH server 3 (200-3) in the network 3 is moved onto the network 2. When the document stored in the client PC 3 (100-3) on the network 2, which is the destination of the movement, is handled, the handling is made possible by communicating with the DH server 3 (200-3).

In addition to this configuration, the system may be configured such that the DH servers provided on the respective networks mutually exchange the handling history information and the identification information for the client PC 100 that is under management, and the identical processing can be implemented even when any of the DH servers is used. According to such configuration, even when the client PC 3 (100-3) is moved from the network 3 onto the network 2, the DH server 2 (200-2) provided in the network 2, which is the destination of the movement, can generate and manage handling history information.

In this case, the DH server 2 (200-2) that prepares handling history information transfers the handling history information to the DH server 1 (200-1) and DH server 3 (200-3), whereby all the DH servers on the network can manage the identical handling history information. In each DH server, the handling history information based on the reference prepared for each document is managed.

The present invention is not limited to the exemplary embodiment described above and illustrated in the drawings, and may be appropriately modified for embodiment without departing from the spirit and scope thereof.

According to the present invention, the document handling history management system that implements the processing described above may be configured such that the document handling history management system having a communication function is caused to implement the operation described above, or a program for configuring the above-described means is installed from a recording medium (CD-ROM, DVD-ROM, etc.) storing the program to a computer, and the computer is caused to implement the program. In the computer that constitutes the document history processing system, the CPU (Central Processor Unit), the ROM (Read Only Memory), the RAM (Random Access Memory), and the hard disk are connected to one another through the system bus. The CPU implements the processing using the RAM as the working area in accordance with the program stored in the ROM or hard disk.

In addition, the medium that supplies the program may also be a communication medium (a medium that temporarily or fluidly holds the program, such as a communication line or a communication system). For example, the program may be provided on the electronic bulletin board (BBS: Bulletin Board Service) on the communication network to be distributed through the communication line.

The present invention is applicable to a system and a program therefor that allow the handling history information to be managed on the basis of the handling contents.

The foregoing description of the exemplary embodiment of the present invention is provided for the purposes of illustration and description. It is not intended to be exhaustive or to limit the invention to the precise forms disclosed. Obviously, many modifications and variations will be apparent to practitioners skilled in the art. The exemplary embodiment was chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A document handling history management system comprising:
    a header rewriting section that stores a set value of a header of a document and changes the header of the document for each access to the document; and
    a first calculation section that calculates a first value for the document by applying a computing equation to the document,
    wherein a microprocessor is programmed to determine whether a type of the access to the document is a non-modifying operation or a modifying operation, and in response to the type of the access being determined as a non-modifying operation, the header of the document that is changed by the header rewriting section is overwritten with the stored set value of the header prior to calculating the first value for the document with the first calculation section, and in response to the type of the access being determined as a modifying operation, the stored set value of the header is discarded prior to calculating the first value.

2. The document handling history management system according to claim 1, wherein the document includes the header, and a body portion comprising content of the document, and the non-modifying operation only causes a change to the header.

3. The document handling history management system according to claim 1, wherein the non-modifying operation is reading or referencing the document.

4. The document handling history management system according to claim 1,
    wherein the header comprises at least one of a time stamp of the document, an apparatus identification of an apparatus that accesses the document, and user identification that identifies an user of the document.

5. A non-transitory computer-readable storage medium with a document handling history management program stored thereon, wherein the program instructs a microprocessor to perform a process, the process comprising:
    accessing a document;
    storing a set value of a header of the document and changing the header of the document for the access to the document;
    calculating a first value for the document by applying a computing equation to the document; and
    determining whether a type of the access to the document is a non-modifying operation or a modifying operation,
    wherein in response to the type of the access being determined as a non-modifying operation, the header of the document that is changed is overwritten with the stored set value of the header prior to calculating the first value for the document, and in response to the type of the access being determined as a modifying operation, the stored set value of the header is discarded prior to calculating the first value.

6. A document handling history management system comprising:
    a header rewriting section that stores a set value of a header of a document and changes the header of the document for each access to the document; and
    a first calculation section that calculates a first value for the document by applying a first computing equation to the document,
    wherein a microprocessor is programmed to determine whether a type of the access to the document is a non-modifying operation or a modifying operation, and in response to the type of the access being determined as a non-modifying operation, the header of the document that is changed by the header rewriting section is overwritten with the stored set value of the header prior to calculating the first value for the document with the first calculation section, and in response to the type of the access being determined as a modifying operation, the stored set value of the header is discarded prior to calculating the first value;
    an operation history information generation section that generates an operation history of the document, the operation history comprising operation history information relating to the access to the document and the first value for the document; and
    a second calculation section that calculates a second value for the operation history of the document by applying a second computing equation to the operation history of the document.

7. The document handling history management system according to claim 6, wherein the operation history of the document further comprises a third value for a previous version of the document, the third value being calculated by applying the second computing equation to the pervious version.

8. The document handling history management system according to claim 6, further comprising:
    a referencing information generation section that generates a reference file for the document, the reference file including the second value for the operation history of the document.

9. The document handling history management system according to claim 6, wherein the operation history information relating to the access to the document comprises at least one of user information of a user who handled the document, time information indicating a time the access occurred, and a type of the access.

10. The document handling history management system according to claim 6, wherein the operation history of the document is generated in a format of extensible markup language (XML).

11. A non-transitory computer-readable storage medium with a document handling history management program stored thereon, wherein the program instructs a microprocessor to perform a process, the process comprising:

accessing a document;

storing a set value of a header of the document and changing the header of the document for the access to the document;

calculating a first value for the document by applying a first computing equation to the document;

generating an operation history of the document, the operation history comprising operation history information relating to the access to the document and the first value for the document;

calculating a second value for the operation history of the document by applying a second computing equation to the operation history of the document; and determining whether a type of the access to the document is a non-modifying operation or a modifying operation, wherein in response to the type of the access being determined as a non-modifying operation, the header of the document that is changed is overwritten with the stored set value of the header prior to calculating the first value for the document, and in response to the type of the access being determined as a modifying operation, the stored set value of the header is discarded prior to calculating the first value.

12. The process according to claim 11, wherein the operation history further comprises a third value for a previous version of the document, the third value being calculated by applying the second computing equation to the previous version.

13. The process according to claim 11 further comprising:

generating a reference file for the document, the reference file including the second value for the operation history of the document.

14. The process according to claim 11, wherein the operation history information relating to the access to the document comprises at least one of user information of a user who handled the document, time information indicating a time the access occurred, and a type of the access.

* * * * *